US00PP26725P2

(12) United States Plant Patent
van Noort

(10) Patent No.: US PP26,725 P2
(45) Date of Patent: May 10, 2016

(54) ***GERANIUM* PLANT NAMED 'NOORTPURPLE'**

(50) Latin Name: *Geranium cinereum*
Varietal Denomination: Noortpurple

(71) Applicant: Marco van Noort, Warmond (NL)

(72) Inventor: Marco van Noort, Warmond (NL)

(73) Assignee: Marco Van Noort Breeding BV, Warmond (NL)

( * ) Notice: Subject to any disclaimer, the term of this patent is extended or adjusted under 35 U.S.C. 154(b) by 8 days.

(21) Appl. No.: 14/544,146

(22) Filed: Dec. 2, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/02; A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium cinereum*, 'Noortpurple', that is characterized by its relatively large flowers that are clear deep purple in color with darker purple veins and consistent in color throughout the plant, its long flower peduncles, and its greater resistance to soil fungi relative to other *Geranium cinereum* cultivars.

2 Drawing Sheets

Botanical classification: *Geranium cinereum.*
Cultivar designation: 'Noortpurple'.

BACKGROUND OF THE INVENTION

The present invention relates to a new and distinct cultivar of *Geranium* plant, botanically known as *Geranium cinereum* 'Noortpurple' and will be referred to hereafter by its cultivar name, 'Noortpurple'.

'Noortpurple' was derived from a breeding program conducted by the Inventor in Warmond, The Netherlands. The objectives of the breeding program were to develop new cultivars of *Geranium cinereum* in a range of flower colors that commence bloom early in the season and exhibit disease resistance, compact plant habits and rain resistance. 'Noortpurple' arose from a cross made in 2010 between an unnamed and unpatented plant of *Geranium cinereum* var. *subcaulescens* from the Inventor's breeding program as the female parent and *Geranium cinereum* 'Laurence Flatman' (not patented) as the male parent. The Inventor selected 'Noortpurple' as a single unique plant amongst the seedlings that resulted from the above cross in May of 2012.

Asexual propagation of the new cultivar was first accomplished by in vitro propagation by the Inventor in Otrebusy, Poland in April of 2014. Asexual propagation by in vitro propagation and root cuttings has determined that the characteristics of the new cultivar are stable and are reproduced true to type in successive generations.

SUMMARY OF THE INVENTION

The following traits have been repeatedly observed and represent the characteristics of 'Noortpurple'. These attributes in combination distinguish 'Noortpurple' as a new and distinct cultivar of *Geranium.*

1. 'Noortpurple' exhibits relatively large flowers that are that are clear deep purple with darker purple veins in color.
2. 'Noortpurple' exhibits long flower peduncles.

3. 'Noortpurple' exhibits greater resistance to soil fungi relative to other *Geranium cinereum* cultivars.
4. 'Noortpurple' exhibits flowers that are consistent in color throughout the plant.

The female parent of 'Noortpurple' differs from 'Noortpurple' in having flowers that are lighter purple in color with less conspicuous veins with peduncles that are shorter in length, and in having a shorter plant height. The male parent of 'Noortpurple', 'Laurence Flatman', differs from 'Noortpurple' in having smaller flowers that are lilac and dark purple in color and in having peduncles that are shorter in length. 'Noortpurple' can also be compared to the *Geranium cinereum* cultivar, 'Purple Pillow' (U.S. Plant Pat. No. 12,829). 'Purple Pillow' is similar to 'Noortpurple' in overall plant shape. 'Purple Pillow' differs from 'Noortpurple' in having flowers that are smaller in size, lighter purple in color and less consistent in color and having peduncles that are shorter in length.

BRIEF DESCRIPTION OF THE DRAWINGS

The accompanying colored photographs illustrate the overall appearance and distinct characteristics of the new *Geranium*. The photographs were taken of a one year-old plant of 'Noortpurple' as field grown in Warmond, The Netherlands and placed in a container for the photographs.

The photograph in FIG. 1 provides an overall view of a plant of 'Noortpurple' in bloom.

Figure 1:
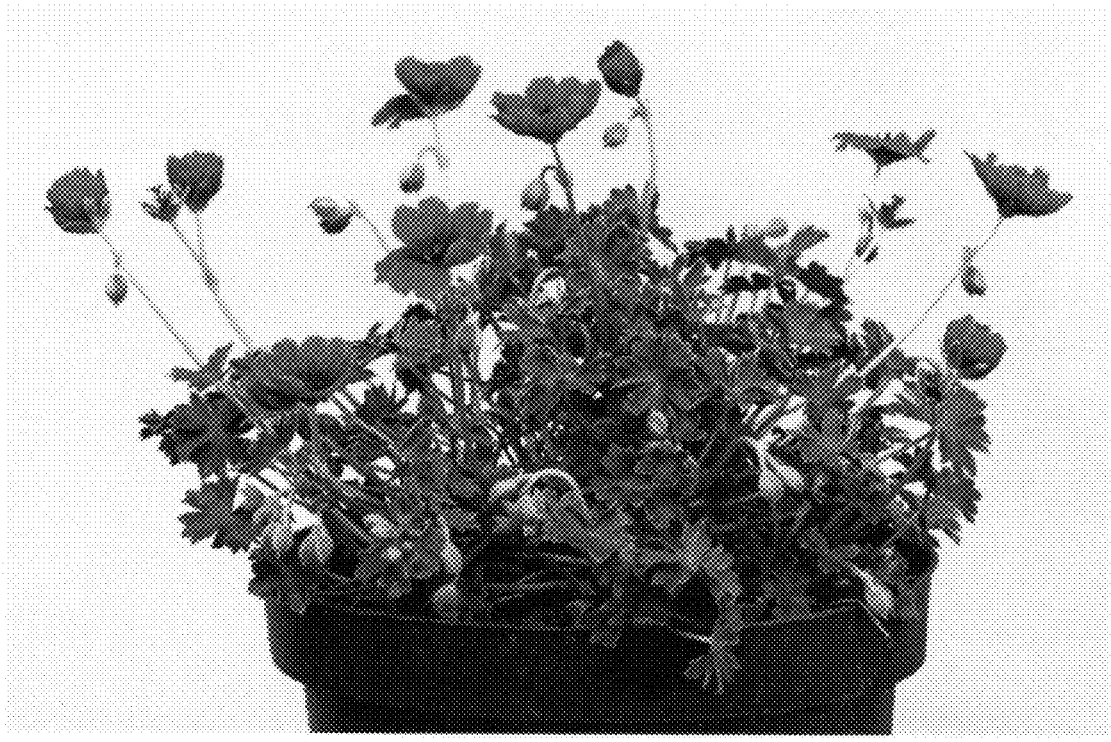
Figure 2:
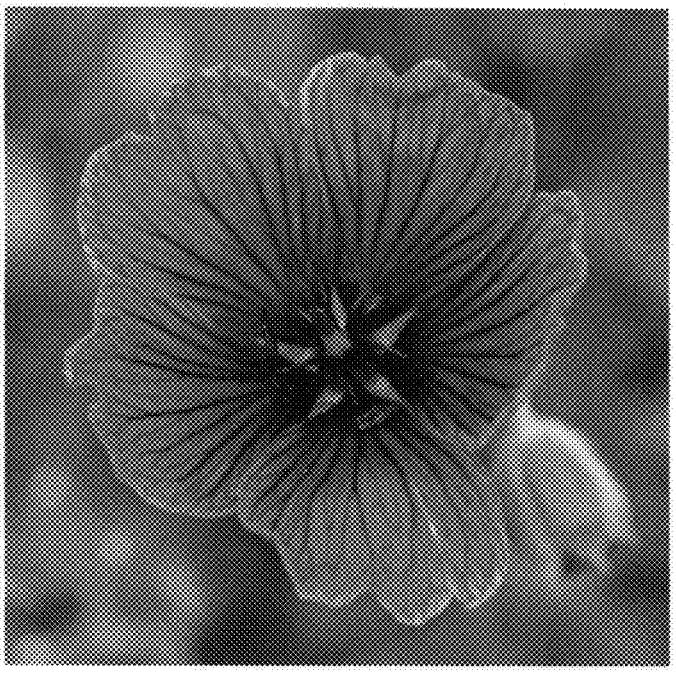

The photograph in FIG. 2 provides a close-up view of a flower of 'Noortpurple'.

Figure 3:
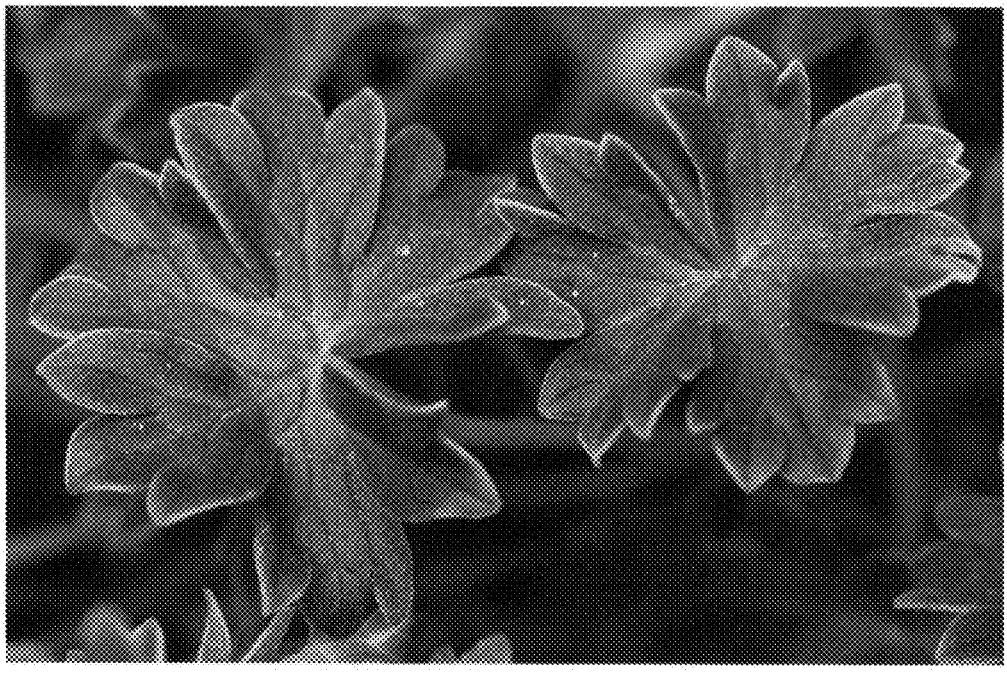

The photograph in FIG. 3 provides a close-up view of the foliage of 'Noortpurple'.

The colors in the photographs are as close as possible with the digital photography techniques available, the color values cited in the detailed botanical description accurately describe the colors of the new *Geranium.*

DETAILED BOTANICAL DESCRIPTION OF THE PLANT

The following is a detailed description of one year-old plants of the new cultivar as field grown in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—April to June in The Netherlands.

*Plant type*.—Herbaceous perennial.

*Plant habit*.—Low growing, spreading, and flattened with flowers held above the foliage.

*Height and spread*.—An average of 20 cm in height and 30 cm in spread as a one year-old plant in the garden.

*Cold hardiness*.—At least to U.S.D.A. Zone 5.

*Diseases*.—Observed to have some resistance to soil fungi caused by *Botrytis cinerea* and *Pythium* spp.

*Root description*.—Fibrous and fine, primarily N167B and N170A in color.

*Root development*.—An average of 20 weeks to fully develop from a rooted cutting in a 9-cm container.

*Growth rate*.—Moderate.

*Propagation*.—In vitro propagation (preferred) and root cuttings.

Stem description:

*Stem size*.—Average of 7.9 cm in length and 2.5 mm in width.

*Stem shape*.—Round.

*Stem color*.—145A, upper side tinged 177D.

*Stem surface*.—Slightly glossy with stems moderately covered with very short soft adpressed hairs; average of 0.5 mm in length and too small to measure color.

*Stem strength*.—Moderately strong.

*Internode length*.—Average of 6.6 cm.

*Branching*.—Moderately branched with an average of 12 lateral branches.

Foliage description:

*Leaf shape*.—Reniform (in outline), palmately deeply cleft to parted with an average of seven lobes.

*Leaf division*.—Simple.

*Leaf base*.—Hastate (free to slightly overlapping).

*Leaf apex*.—Abruptly acute.

*Leaf venation*.—Palmate, upper and lower side 143A.

*Leaf margins*.—Palmately deeply cleft to parted into an average of seven lobes, margins of lobes incised.

*Leaf attachment*.—Petiolate.

*Leaf arrangement*.—Opposite.

*Leaf surface*.—Upper side slightly glossy, lower side matte, both sides moderately covered with short and soft adpressed hairs, average of 0.5 mm in length and too small to measure color.

*Leaf size*.—Average of 2.9 cm in length and 3.1 cm in width.

*Leaf color*.—Upper surface young; N137A, lower surface young; 137B, upper surface mature; color between N137C and 139A, lower surface mature; 137C.

*Leaf quantity*.—Average of 4 leaves per lateral branch.

*Petioles*.—Average of 8.3 cm in length and 1 mm in diameter, 144B in color, surface puberulent.

*Stipules*.—2 leafy stipules are present at the base of the leaves, narrow deltoid in shape, narrow acuminate apex, truncate base, average of 1 cm in length and 3 mm in width, color; both surfaces 145C to 145D, both surfaces puberulent.

Flower description:

*Inflorescence type*.—Single, rotate flowers, arranged in pairs.

*Lastingness of flowers*.—About 7 days on the plant, sepals persistent.

*Flower size*.—Average of 1.7 cm in height and 3.6 cm in diameter.

*Flower fragrance*.—None.

*Flower number*.—Average of 8 flowers and bud per lateral system, average of 124 per plant.

*Flower aspect*.—Upright to slightly outward.

*Flower buds*.—Broad elliptic to broad obovate in shape, average of 9 mm in length and up to 6 mm in diameter, 138B in color with veins N137A, surface densely covered with short soft hairs 1 mm in length and NN155D in color.

*Corolla features*.—Petals are unfused and arranged in a rotate form, slightly cupped.

*Petal number*.—5.

*Petal shape*.—Obcordate.

*Petal color*.—When opening upper surface; N74A, base tinged 72A, veined N186A, when opening lower surface; N74A, veined N186C, fully open upper surface; N74A, base a color between 71A and 72A, veined N186A, fully open lower surface; 72A, base 71A, veined N186C.

*Petal surface*.—Both sides matte and velvety.

*Petal margins*.—Entire with retuse apex.

*Petal apex*.—Retuse.

*Petal size*.—Average of 1.9 cm in length and 1.7 cm in width.

*Calyx*.—Rotate and cupped, 6 mm in length and 1.7 cm in diameter.

*Sepals*.—5, ovate in shape, average of 1 mm length and 4 mm in width, entire margin, mucronate apex, cuneate base, both surfaces matte, color; young upper surface; 143A, young lower surface; 138A to 138B, mature upper surface; 143A, mature lower surface; 138A to 138B.

*Peduncles*.—Round in shape, average of 11.8 cm in length and 1 mm in diameter, strong, held at a 35° angle to the lateral branch, color of surfaces are 145A, upper surface (sun exposed) can be tinged with 177D, surface puberulent.

*Pedicels*.—Round in shape, average of 1.6 cm in length and 1 mm in diameter, strong, one flower straight on top of peduncle, the second flower held in an average angle of 35° to lateral branch, color of surfaces are 144A, surface puberulent.

Reproductive organs:

*Gynoecium*.—1 pistil, average of 7 mm in length, 5 stigmas are decurrent (reflexed) and 187A in color, style is an average of 4 mm in length and 143A in color, ovary is 143A in color.

*Androecium*.—10 stamens, anthers are dorsifixed, oblong in shape and held at a 90° angle on top of filament, 25 mm in length, and 203A in color, filaments are 5 mm in length and N186C in color, pollen is moderate in quantity and 10A in color.

*Fruit/seeds*.—None detected.

It is claimed:

1. A new and distinct cultivar of *Geranium* plant named 'Noortpurple' as herein illustrated and described.

* * * * *